(12) United States Patent
Shifflette

(10) Patent No.: US 9,028,392 B2
(45) Date of Patent: May 12, 2015

(54) MEDICAL DEVICE

(75) Inventor: J. Michael Shifflette, Alachua, FL (US)

(73) Assignee: NuCardia, Inc., El Dorado Hills, CA (US)

( * ) Notice: Subject to any disclaimer, the term of this patent is extended or adjusted under 35 U.S.C. 154(b) by 1648 days.

(21) Appl. No.: 11/565,969

(22) Filed: Dec. 1, 2006

(65) Prior Publication Data

US 2008/0132747 A1 Jun. 5, 2008

(51) Int. Cl.
*A61M 1/12* (2006.01)
*A61M 1/10* (2006.01)

(52) U.S. Cl.
CPC ............ *A61M 1/101* (2013.01); *A61M 1/1034* (2014.02); *A61M 1/125* (2014.02)

(58) Field of Classification Search
CPC ...... A61M 1/101; A61M 1/122; A61M 1/125
USPC ...................................... 604/16, 151; 607/16
See application file for complete search history.

(56) References Cited

U.S. PATENT DOCUMENTS

| | | |
|---|---|---|
| 4,625,712 A | 12/1986 | Wampler |
| 4,753,221 A | 6/1988 | Kensey |
| 4,817,586 A | 4/1989 | Wampler |
| 4,846,152 A | 7/1989 | Wampler et al. |
| 4,919,647 A | 4/1990 | Nash |
| 5,092,844 A | 3/1992 | Schwartz et al. |
| 5,169,378 A | 12/1992 | Figuera |
| 5,376,114 A | 12/1994 | Jarvik |
| 5,405,383 A | 4/1995 | Barr |
| 5,588,812 A | 12/1996 | Taylor et al. |
| 5,749,855 A * | 5/1998 | Reitan ........................ 604/151 |
| 5,755,784 A | 5/1998 | Jarvik |
| 5,776,190 A | 7/1998 | Jarvik |
| 5,888,241 A | 3/1999 | Jarvik |
| 6,007,478 A | 12/1999 | Siess et al. |
| 6,058,593 A | 5/2000 | Siess |
| 6,139,487 A | 10/2000 | Siess |
| 6,176,822 B1 | 1/2001 | Nix et al. |
| 6,176,848 B1 | 1/2001 | Ran et al. |
| 6,200,260 B1 | 3/2001 | Bolling |

(Continued)

FOREIGN PATENT DOCUMENTS

| | | |
|---|---|---|
| WO | 9639956 A1 | 12/1996 |
| WO | 0121249 A1 | 3/2001 |

(Continued)

OTHER PUBLICATIONS

Hochrein, Marion, "PCT Application No. PCT/US2007/086876 International Preliminary Report on Patentability Mar. 24, 2010",, Publisher: PCT, Published in: PCT.

(Continued)

*Primary Examiner* — Christopher D Koharski
*Assistant Examiner* — Michael D Abreu
(74) *Attorney, Agent, or Firm* — Kaplan Breyer Schwarz & Ottesen, LLP

(57) ABSTRACT

A temporary cardiac-assist device is disclosed. The device includes a pump assembly that is deployed in the ascending aorta or the heart. A torque transmission line couples the pump assembly to an external motor for driving impeller blades within the pump assembly. The pump assembly expands in size at its destination site for operation. In operation, neither the torque transmission line nor elements that support the impeller blades are under axial forces.

26 Claims, 8 Drawing Sheets

(56) References Cited

U.S. PATENT DOCUMENTS

| | | |
|---|---|---|
| 6,227,820 B1 | 5/2001 | Jarvik |
| 6,245,007 B1 | 6/2001 | Bedingham et al. |
| 6,299,575 B1 | 10/2001 | Bolling |
| 6,387,037 B1 | 5/2002 | Bolling et al. |
| 6,406,422 B1 | 6/2002 | Landesberg |
| 6,428,464 B1 | 8/2002 | Bolling |
| 6,497,698 B1 | 12/2002 | Fonger et al. |
| 6,508,787 B2 * | 1/2003 | Erbel et al. .................... 604/151 |
| 6,527,699 B1 | 3/2003 | Goldowsky |
| 6,533,716 B1 | 3/2003 | Schmitz-Rode et al. |
| 6,544,216 B1 | 4/2003 | Sammler et al. |
| 6,620,004 B1 | 9/2003 | Piper |
| 6,623,475 B1 | 9/2003 | Siess |
| 6,644,125 B1 | 11/2003 | Siess et al. |
| 6,685,621 B2 | 2/2004 | Bolling et al. |
| 6,685,696 B2 | 2/2004 | Fleischhacker et al. |
| 6,716,157 B2 | 4/2004 | Goldowsky |
| 6,719,720 B1 | 4/2004 | Voelker et al. |
| 6,790,171 B1 | 9/2004 | Griindeman et al. |
| 6,794,789 B2 | 9/2004 | Siess et al. |
| 6,808,483 B1 | 10/2004 | Ortiz et al. |
| 6,889,082 B2 | 5/2005 | Bolling et al. |
| 6,942,611 B2 | 9/2005 | Siess |
| 7,011,620 B1 | 3/2006 | Siess |
| 7,022,100 B1 | 4/2006 | Aboul-Hosn et al. |
| 7,070,555 B2 | 7/2006 | Siess |
| 7,258,679 B2 | 8/2007 | Moore et al. |
| 7,371,210 B2 | 5/2008 | Brock et al. |
| 7,393,181 B2 | 7/2008 | McBride et al. |
| 2003/0105383 A1 | 6/2003 | Barbut et al. |
| 2003/0163019 A1 | 8/2003 | Goldowsky |
| 2004/0241019 A1 | 12/2004 | Goldowsky |
| 2005/0049696 A1 | 3/2005 | Siess |
| 2006/0008349 A1 | 1/2006 | Khaw |
| 2008/0103591 A1 | 5/2008 | Siess |
| 2008/0114339 A1 | 5/2008 | McBride et al. |

FOREIGN PATENT DOCUMENTS

| | | |
|---|---|---|
| WO | 0139817 A2 | 6/2001 |
| WO | 0174419 A1 | 10/2001 |
| WO | 0241935 | 5/2002 |
| WO | 0243791 A1 | 6/2002 |
| WO | 0245775 A2 | 6/2002 |
| WO | 03103745 A2 | 12/2003 |
| WO | 2006051023 A1 | 5/2006 |
| WO | 2007112033 A2 | 10/2007 |

OTHER PUBLICATIONS

Norbert Hiesch, "International Patent Application No. PCT/US2007/086876 International Search Report and Written Opinion", Sep. 2, 2008, Publisher: PCT, Published in: PCT.

* cited by examiner

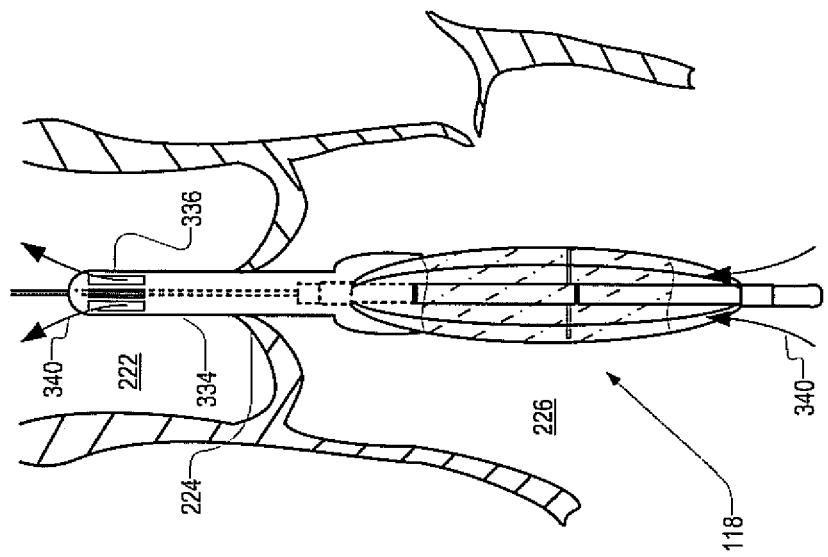
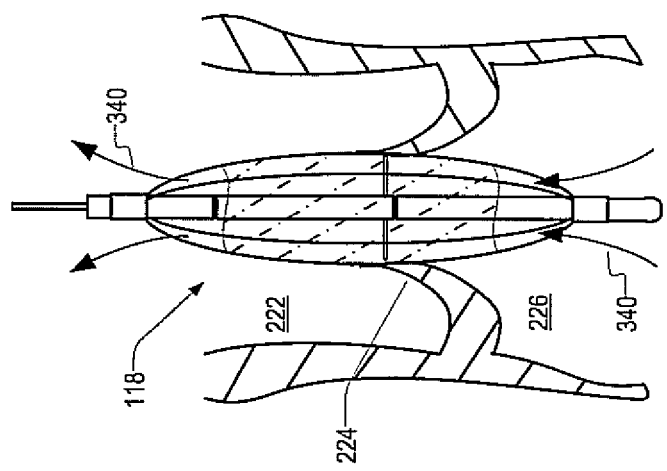
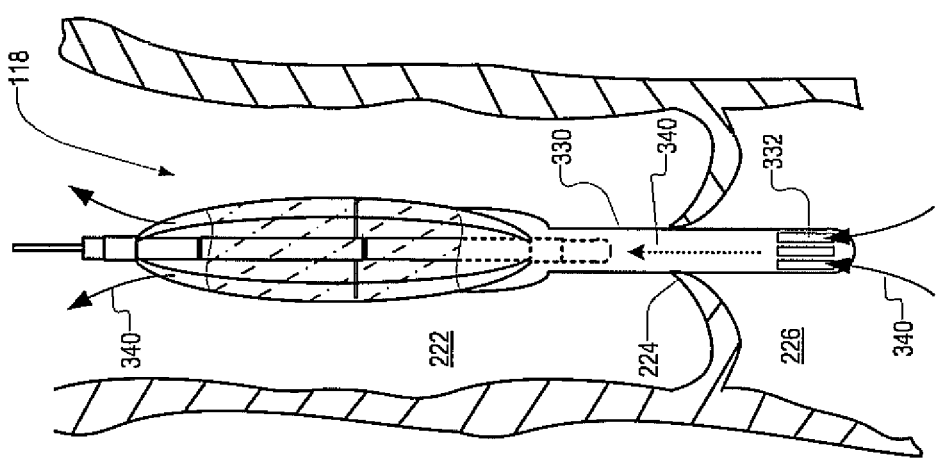
FIG. 3C
FIG. 3B
FIG. 3A

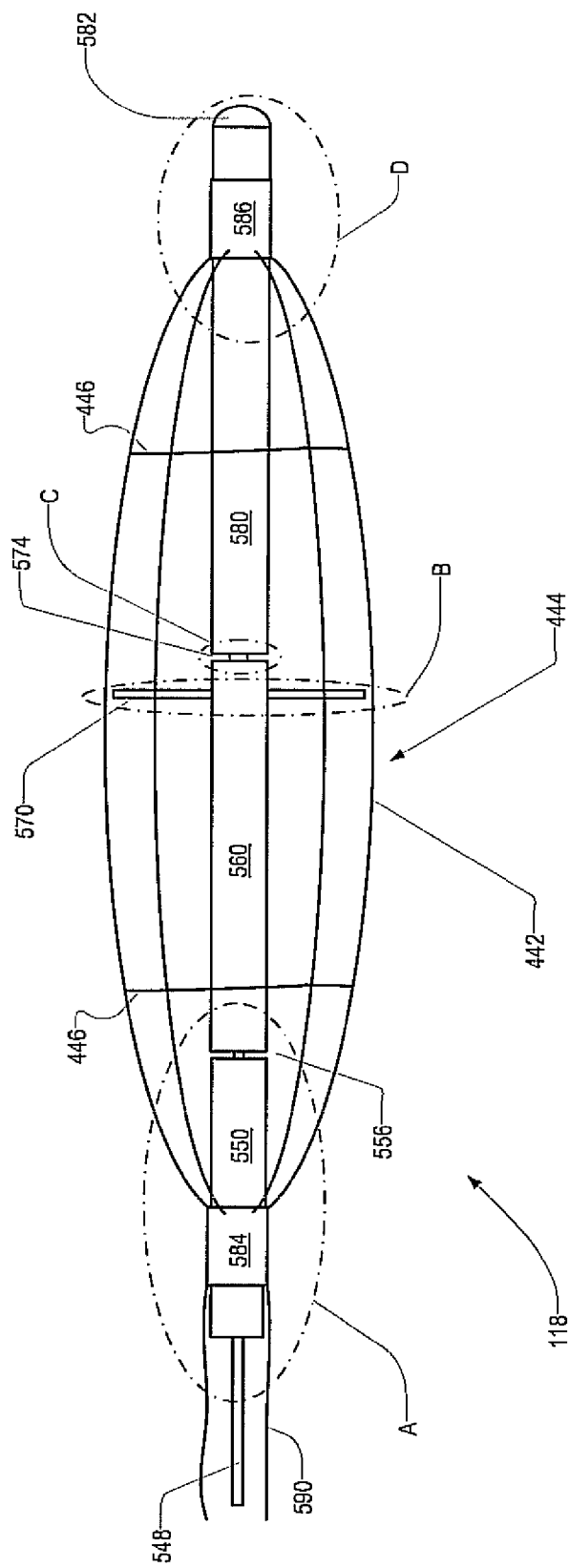

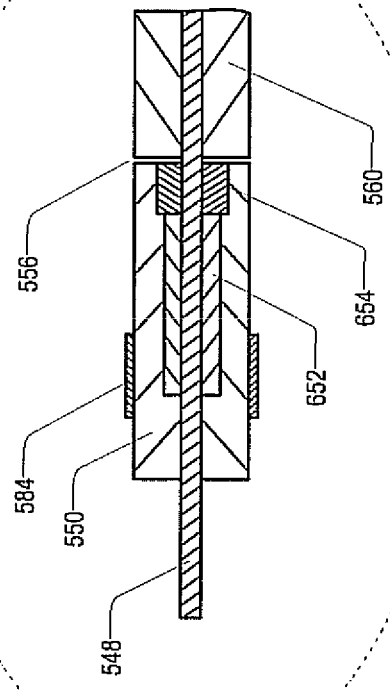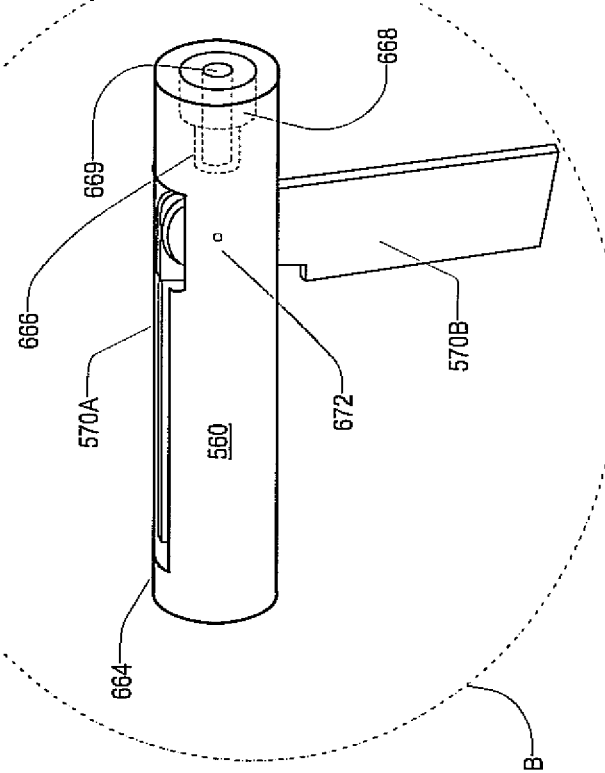

MEDICAL DEVICE

FIELD OF THE INVENTION

The present invention relates to cardiac-assist devices in general, and, more particularly, to blood pumps suitable for percutaneous insertion into the vascular system.

BACKGROUND OF THE INVENTION

Acute heart failure is the sudden inability of the heart to fill with or pump a sufficient volume of blood. The afflicted patient may become weak and short of breath and, in some instances, die. In the most severe acute heart failure episodes, the patient may suffer from cardiogenic shock, a condition that is associated with high reported mortality rates.

Acute heart failure occurs in a variety of contexts. For example, some patients who are hospitalized for Acute Coronary Syndrome (i.e., heart attack and unstable angina) develop acute heart failure. Furthermore, some open-heart surgery patients develop acute heart failure. Acute heart failure also complicates certain illnesses. Additionally, some patients who undergo a Percutaneous Coronary Intervention or other procedure are at risk for developing acute heart failure or dying.

Acute heart failure does not necessarily progress to chronic heart failure or death; recovery is possible. Many patients who have acute heart failure and those at risk for developing it receive interventions that are intended to temporarily assist the heart during a recovery period. The intervention typically lasts for less than a week, but may last longer.

These interventions may include pharmaceuticals and medical devices, including cardiac-assist devices. When these cardiac-assist devices include a pump that supplements the heart's pumping action, they often are referred to as "blood pumps." An effective cardiac assist device assumes some of the heart's pumping function, thereby unloading the heart and enabling it to recover. Cardiac-assist devices and blood pumps can be temporary or permanent.

The most common temporary cardiac-assist device is the intra-aortic balloon pump ("IABP"). An IABP is an inflatable balloon attached to a catheter. The IABP is inserted percutaneously (minimally invasively) into a peripheral vessel and advanced to the descending aorta. When the balloon inflates, it increases blood flow to the coronary arteries. When it deflates, it decreases the pressure against which the heart must pump. The IABP does not, however, increase the cardiac output significantly and a substantial percentage of cardiogenic shock patients that are implanted with IABPs die.

Other temporary cardiac-assist devices include extracorporeal (outside the body) blood pumps. Some of these devices require cardiac surgeons to connect them to the patient's heart and blood vessels directly through the exposed chest using "cannulas," which are relatively large-diameter tubes. Such procedures are considered invasive, may require cardiopulmonary bypass, and are associated with significant complications. Some other extracorporeal blood pumps are connected to the patient using relatively wide catheters or cannulas that are inserted through peripheral blood vessels. Certain of these devices do not increase the heart's output significantly, are difficult to use, and/or are associated with significant complications.

Emerging data indicate that temporary, percutaneously-inserted blood pumps may provide an alternative to IABPs as well as extracorporeal blood pumps and other cumbersome devices. When these temporary blood pumps are attached to a catheter, they are known as "catheter blood pumps." Some catheter blood pumps are inserted using established cath-lab techniques. These techniques are less invasive than cardiac surgery or other relatively complicated procedures.

Notwithstanding its attractiveness as a less-invasive alternative, certain percutaneously-inserted blood pumps exhibit one or more of the following drawbacks, in addition to any other shortcomings:

limited pump flow;

some degree of hemolysis (i.e., destruction of red blood cells);

require the use of a large catheter/cannula, with a risk of ischemia; and relatively high cost.

The limited pump flow results from the fact that to be inserted percutaneously, the blood pump must be quite small. In particular, it is desirable for the blood pump to have a 12 French (4 millimeter) or smaller catheter.

Hemolysis can result when blood comes into contact with rapidly rotating elements.

One approach in the prior art to the size/flow challenge is the "expandable" blood pump. This pump, which is suitably small for percutaneous insertion, expands once in place within the vasculature or the heart. Although interesting conceptually, the expandable blood pump has proven to be difficult to implement. The pumps disclosed in U.S. Pat. Nos. 4,753,221, 5,749,855, and 6,981,942 are representative of the expandable blood pump and the problems of its implementation.

The pump that is disclosed in the '221 patent includes a catheter having an expandable propeller that is disposed in its distal end. When the propeller is deployed for operation, it spans a distance that is greater than the diameter of the catheter. To deploy the propeller, therefore, the distal end of the catheter must be enlarged. For that purpose, the distal end of the catheter is formed from a flexible material that is capable of expanding outward to provide a flared, enlarged-diameter region that can accommodate the propeller. The end of the catheter is enlarged by inflating a balloon that is disposed on the exterior of the catheter, just proximal to the flexible region. In particular, the tension on the distal end of the catheter resulting from the inflating balloon causes the enlargement.

Depending upon the orientation of the pump within the heart, blood is either: (1) drawn through the catheter and expelled at its distal end (near the pump), or (2) drawn in at the distal end of the catheter near the propeller, pumped through a length of the catheter, and then expelled through orifices. In either case, pumping the blood through the relatively smaller diameter catheter substantially defeats the purpose of providing an expandable pump. The region for flow must be expanded, as well as the propeller, to reap the benefits of increased flow.

The pump that is disclosed in the '855 patent has a drive cable that is surrounded, near its distal end, by an expandable cage. The distal end of the drive cable terminates in a spherical protuberance or "ball." This ball is received in a socket that is formed in the distal end of the cage. This ball and socket arrangement serves as the distal bearing of the pump. The proximal end of the cage merges into a sleeve that surrounds the drive cable. In the absence of an applied, axially-directed force, the cage remains in a collapsed state. In this state, the cage has a cylindrical form that closely surrounds the drive cable and enables the pump to be inserted into a catheter.

An outwardly foldable propeller depends from the drive cable a short distance from its distal end. In the absence of an applied, axially-directed force, the propeller remains folded flat against the drive cable. The drive cable consists of an inner part (which extends distal to the propeller and terminates in the ball, as discussed above) and an outer part (which ends at the propeller). The drive cable is designed so that its inner part is movable relative to its outer part. As the inner part of the drive cable is drawn in the proximal direction by an axially-applied force (e.g., by a medical practitioner tugging on the inner part), relative movement between the inner and outer parts of the drive cable expands the propeller. At the same time, and by virtue of the same applied force, relative movement between the sleeve and the outer part of the drive cable expands the cage. The deployed propeller can then freely spin within the expanded cage.

While this pump overcomes the aforementioned flow-restriction problem with the '221 patent, it suffers from several other significant drawbacks. One drawback pertains to its distal bearing. This bearing, which stabilizes the propeller within the expandable cage, is implemented as a thrust bearing. That is, in operation of the pump, the bearing is placed in tension as the inner part of the drive cable is moved axially (and subsequently held in place) to expand the cage and propeller. It will be appreciated that under tension, this bearing is difficult to seal. And any blood that enters the space between the ball (which is rapidly spinning since the cable is spinning) and the socket will be hemolyzed and otherwise disrupted, making this bearing a likely site for thrombosis. Furthermore, the sliding friction between the ball and socket results in heat and wear. The heat can damage the blood and the wear can generate particulates.

A second shortcoming with the blood pump that is disclosed in the '855 patent relates to the fact that the drive cable experiences an axial load (to keep the cage expanded). This axial load increases the severity of wear between the drive cable and the surrounding catheter since both will be generally non-rectilinear (and thus establish loci of high surface contact pressure) to reach the heart from the insertion point at the femoral artery.

A third drawback of this blood pump is that it requires at least three seals: one for the distal bearing, a second for the two-part drive cable, and a third for the sleeve and outer part of the drive cable. Every seal presents a possibility for leakage of blood past the seal, which can ultimately result in hemolysis and thrombosis.

A third prior-art blood pump, as disclosed in the '942 patent, expands via inflation. In particular, the pump includes an inflatable propeller and a surrounding inflatable housing. As the housing inflates, it expands outwardly as well as inwardly. Since there appears to be nothing to restrict inward expansion of the housing, the inflated housing and the inflated propeller are likely to come into contact with one another. Contact between the rotating propeller and the housing could interfere with proper pumping function.

The problems with prior-art expandable blood pumps, as exemplified by the shortcomings of the three devices discussed above, limit their potential utility as a life-sustaining device. As a consequence, cardiac specialists and the patients that they treat would benefit from improvements to percutaneously-inserted, expandable blood pumps.

SUMMARY OF THE INVENTION

The present invention provides a way to temporarily assist the heart by supplementing the heart's pumping action without some of the costs and disadvantages of the prior art.

The illustrative embodiment of the invention is a percutaneously-inserted, expandable, cardiac-assist device. While the illustrative embodiment is intended to be for temporary use, it is possible to modify it for longer-term or permanent use.

In accordance with the illustrative embodiment, the cardiac-assist device includes a pump assembly that is deployed in the ascending aorta or the heart. In some other embodiments, however, other deployment sites may suitably be used (e.g., the descending aorta, peripheral blood vessels, even right-side locations, etc.). A torque transmission line couples the pump assembly to an extracorporeal motor. The motor, via the transmission line, drives impeller blades within the pump assembly.

Since the pump assembly is percutaneously inserted, it is advantageously sized so that it can be introduced into the vascular system (e.g., Femoral artery, etc.) via a 12-French or smaller-diameter. Historically, it has been difficult to achieve average flows greater than about 2 to 2.5 liters per minute against physiologic pressures through a 12-French catheter, which has a diameter of 4 millimeters. To that end, the pump assembly expands when it reaches its intended deployment site.

In some embodiments, the pump assembly is deployed in a patient as follows:
  An introducing tube (e.g., catheter, sheath, etc.) is inserted in the vascular system of a patient and its distal end is advanced to a location just beyond the aortic arch.
  After the second end of the introducing tube is in position beyond the aortic arch, the pump assembly is inserted into the proximal (extracorporeal) end of the tube.
  The pump assembly is advanced through the introducing tube to its distal end.
  The pump assembly is deployed by exiting the distal end of the introducing tube.

It is notable that this method can suitably be used to deploy cardiac-assist devices other than those disclosed herein, assuming that they are of suitable size. In fact, the method can be used to deploy medical devices that are not necessarily cardiac-assist devices. Furthermore, this method can be used for deployment to other locations than the ascending aorta or the heart. To the extent that the pump assembly is intended for such other locations, the various operations listed above are suitably modified, as necessary. That is, if the pump assembly is to be deployed in the descending aorta, for example, it will be understood that the introducing tube need not be "advanced to a location just beyond the aortic arch."

The pump assembly generally comprises two components: an impeller (with associated support members) and a casing. The casing is an important feature because it channels flow toward and away from the impeller, among other functions.

The pump assembly of the illustrative embodiment includes several axially-located and linearly-arranged elements including: a proximal support housing, an impeller hub, and a distal support. These elements are the aforementioned impeller support members. The torque transmission line, which is embodied as a drive shaft (in the immediate vicinity of the pump assembly), passes through the proximal support housing and is rigidly fixed to the impeller housing. Collapsible impeller blades depend from the impeller hub. Through this arrangement, the rotating drive shaft drives the impeller hub which, in turn, drives the impeller blades. When deployed and in operation, the rotating impeller blades delimit a circle ("the blade circle") having a diameter that exceeds the pump assembly's collapsed diameter by a factor that is typically within the range of about 2 to about 7, and more typically within a range of 3 to 5. These ranges are provided for the purpose of illustration, not limitation. Mechanical considerations aside, the anatomical environment of the deployed pump assembly influences the maximum theoretical enlargement factor.

A plurality of spaced-apart, rib-like elements collectively defines the casing that surrounds the impeller blades, impeller hub, and a portion of the proximal and distal supports. The casing is reconfigurable between two states: an expanded (diameter) state and a contracted (diameter) state.

In the expanded state, each rib typically has a curved, non-planar, or non-rectilinear shape. The expanded state enables the casing to accommodate the deployed impeller blades. In the illustrative embodiment, the ribs adopt an arcuate shape when in the expanded state, wherein they collectively define a substantially ellipsoid-shape casing. In other embodiments, the ribs have other non-planar shapes when in the expanded state.

In the contracted state, the ribs are substantially straight or planar and virtually in contact with the axially-aligned elements (e.g., the impeller housing, etc.). In the contracted state, the casing has its minimum diameter and exhibits a cylindrical shape. For some embodiments, the contracted state enables the pump assembly to be inserted into a 12-French or smaller introduction catheter to ease deployment within the vascular system. A membrane is disposed on a portion of the casing to provide a flow-channeling function, as previously mentioned.

It is notable that, in the illustrative embodiment, the rotating impeller hub is flanked by non-rotating supports: the proximal support housing and the distal support. The proximal support housing receives a proximal support ring that is the terminus of the proximal end of the casing-defining ribs. The distal support receives a distal support ring that is terminus of the distal end of the ribs. In some embodiments, one of the two support rings is configured to be movable in the axial direction while the other support ring is non movable. In some embodiments, movement in the axial direction of the one movable ring enables the casing to expand and contract.

The illustrative embodiment provides a number of advantages in comparison to the prior-art blood pumps that were discussed in the Background section. These include, among any others:
  A. The removal of any axial forces to the drive cable/drive shaft for opening and closing the casing.
  B. A casing that enlarges in the absence of applied force.
  C. A more flexible assembly that is better able to negotiate the aortic arch.
  D. A distal support that, unlike the prior art, is not rotating, such that it is better able to bear the bending loads of the casing.

These advantages are discussed more fully below.

Regarding point A, the blood pump disclosed in the '855 patent applied an axial force directly to the drive cable/drive shaft to expand the surrounding cage. In the illustrative embodiment of the present invention, no axial forces are applied to the drive cable/drive shaft to expand or contract the casing. Compared to the pump disclosed in the '855 patent, the removal of this axial force in the illustrative embodiment results in:
  1. Reduced stress on the drive cable, which provides one or more of the following benefits:
    a. An increase in cable life.
    b. An increases in sheath life by diminishing the cable/sheath contact forces, wear, particulates, and heat generation.
    c. Simplification of the drive cable/shaft to a single component (rather than the inner/outer coaxial arrangement disclosed in the '855 patent).
    d. Elimination of axial displacements between the drive cable, impeller hub, and bearing, which are inherently more difficult to provide bearing support for and to seal.
    e. Permits the drive cable to be terminated at the impeller hub, thereby:
      (i) enabling improved bearing and seal configurations;
      (ii) avoiding an additional rotating component in blood contact; and
      (iii) reducing the number of seals from three to two.
  2. Reduced load on the distal bearing and seal, which provides one or more of the following benefits:
    a. Eliminates the thrust load, thereby:
      (i) diminishing power losses to friction; and
      (ii) simplifying bearing design.
    b. Reduces the radial and bending load on the distal bearing since in the illustrative embodiment, the distal bearing is only required to hold the casing stationary.

Regarding point B, the prior art blood pumps required some actuation step to enlarge the casing. In contrast, the illustrative embodiment incorporates a casing that is open unless a restraining force is applied. In comparison to the prior art, the natural bias to the enlarged state enables:
  1. The use of external forces to contract the casing, such as:
    a. A radial compressive force, as provided by an integral sheath or separate catheter.
    b. An axial tensile force, such as provided by an integral sheath, wires, or cable that couples to the casing to contract it.
  2. The external forces are only required for delivery, but not for deployment and operation. The pump assembly can therefore be operated in a state that is free of axial external forces:
    a. Only rotational forces are involved (the spinning of the impeller);
    b. In the absence of axial forces, the drive cable/drive shaft is free to "float" within the sheath, thereby minimizing contact pressure, friction, and particulate generation.

Regarding point C—the elimination of the axial forces on the central drive cable—a relatively more flexible assembly can therefore be employed. This flexibility simplifies the process of negotiating the vascular system to deploy the pump assembly within a cardiac patient. It is notable that the drive cable does not experience axial forces during insertion and deployment, operation, or withdrawal.

Regarding point D, the stationary distal support of the illustrative embodiment is better able to bear the bending loads of the casing than the rotating distal support of that is disclosed in the '855 patent. Furthermore, the distal support of the illustrative embodiment is the full diameter of the impeller hub, which enhances stability.

BRIEF DESCRIPTION OF THE DRAWINGS

FIGS. 3A-3C depict alternative placement locations for pump assembly.

FIG. 5 depicts further detail of the pump assembly.

FIG. 6A depicts further detail of region "A" of the pump assembly shown in FIG. 5.

FIG. 6B depicts further detail of region "B" of the pump assembly shown in FIG. 5.

DETAILED DESCRIPTION

The following terms are defined for use in this Specification, including the appended claims:

Distal means relatively further from a first end of a torque transmission line that connects a motor to a pump assembly in cardiac-assist device 110. The motor is located at the first (proximal) end of the torque transmission line.

Proximal means relatively closer to the first end of the torque transmission line.

Proximate means "near to."

Axial means an axis or direction that is coincident with a centerline (of a device) and contrary to "radial."

Operatively coupled means that the operation of one device affects another device. For example, if a drive cable is "operatively coupled" to an impeller, it is capable of driving the impeller (i.e., causing the impeller to rotate). Operatively coupled devices need not be directly physically coupled.

Other definitions may be provided later in this disclosure.

Figure 1:
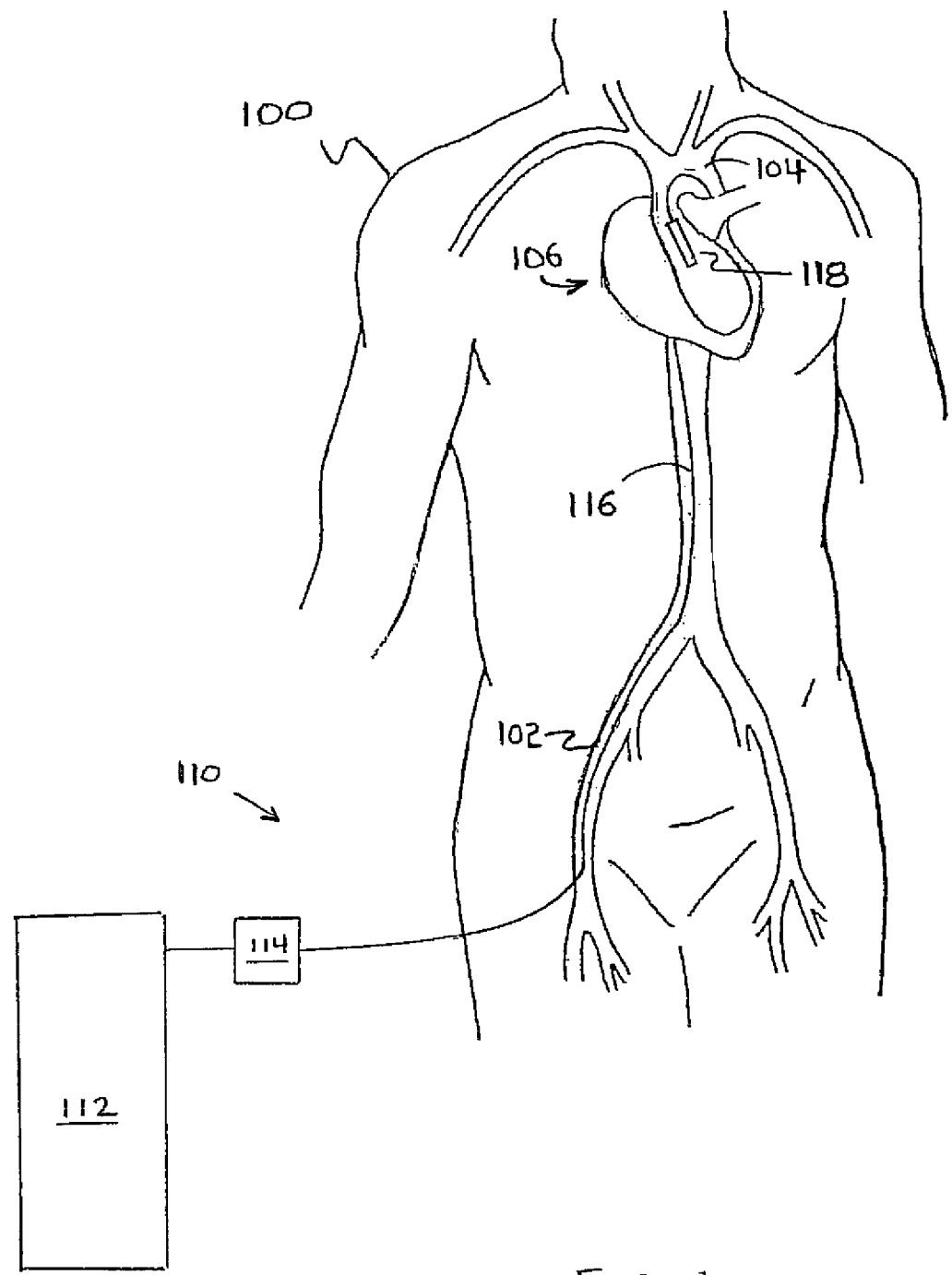
FIG. 1 depicts a partial view of the human body, showing the femoral artery leading to the heart and the placement within the body of pump assembly component 118 of cardiac-assist device 110 in accordance with the illustrative embodiment of the present invention.

FIG. 1 depicts a silhouette of human torso 100. Heart 106 and some internal vasculature (i.e., femoral artery 102, aorta 104, etc.) are shown within torso 100. This Figure also shows portions of cardiac-assist device 110 deployed in torso 100.

The cardiac-assist device 110 comprises controller 112, motor 114, torque-transmission line 116, and pump assembly 118. In use, some elements of cardiac-assist device 110 are extracorporeal (i.e., remain outside of the patient) and others are internally deployed. More specifically, controller 112 and motor 114 remain outside of the body while the bulk of torque transmission line 116 and pump assembly 118 are deployed within the body.

Controller 112 is the human interface of cardiac-assist device 110. The controller, which incorporates a microprocessor, typically provides one or more of the following functions, in addition to any others:

electrical drive for the pump;

optional fluid infusion for lubrication and for a pressurized sealing system;

monitors system performance;

displays impeller speed and pump flow; and provides auditory and visual alerts.

Motor 114 drives pump assembly 118. In some embodiments, motor 114 is a brushless DC servomotor with speed detection and regulation. In some embodiments, motor 114 is suitable for driving pump assembly 118 to provide an average pump flow of 2.5 or more liters per minute at 60 mm Hg average pressure differential across the pump at a fluid viscosity of about 4 cP at 37° C. It will be recognized that the specific power output requirement of motor 114 will be dependent on impeller design (i.e., pump efficiency) and the diameter of the delivery system, among other factors. Those skilled in the art will know how to specify a motor as a function of system design and performance requirements.

Torque transmission line 116 operatively couples motor 114 to pump assembly 118, thereby transmitting motor torque to the pump assembly. Torque transmission line 116 will rotate at a speed in excess of 1000 rpm and possibly as high as 50,000 rpm.

As described in further detail later in this specification, in some embodiments, torque transmission line 116 comprises a flexible drive cable and a rigid drive shaft, the former leading directly to the latter. Substantially all of torque transmission line 116 is the flexible drive cable; this flexibility is required to negotiate the vascular system. The flexible drive cable transitions to rigid drive shaft in the immediate vicinity of pump assembly 118. The flexible and rigid portions of the torque transmission line can be "spliced" together via any of a variety of suitable known techniques, including, without limitation, swaging, via hypo tube and adhesive. In some embodiments, both the cable and the shaft are formed from stainless steel or other suitable metal.

Pump assembly 118 includes a rotating impeller that is driven by torque transmission line 116. The rotating impeller is capable of supplementing native cardiac output by inducing flow through pump assembly 118. As described later in this specification, the rotating impeller and surrounding casing are expandable.

Cardiac-assist device 110 is percutaneously implanted. In some embodiments, known catheterization techniques (e.g., Seldinger, etc.) are used to introduce pump assembly 118 into femoral artery 102, advance it to aorta 104, and then to its intended placement site. As discussed later in conjunction with FIGS. 3A-3C, several placement locations for pump assembly 118 are preferred. These sites include the ascending aorta, across the aortic valve, and within the left ventricle. Pump assembly 118 can be sited elsewhere, such as, without limitation, in the descending aorta, in suitably-sized peripheral blood vessels, or even in the right side of the heart or in right-side-related vasculature. At such alternate locations, one or more modifications are required to the illustrative embodiment, as described further below.

Figure 2:
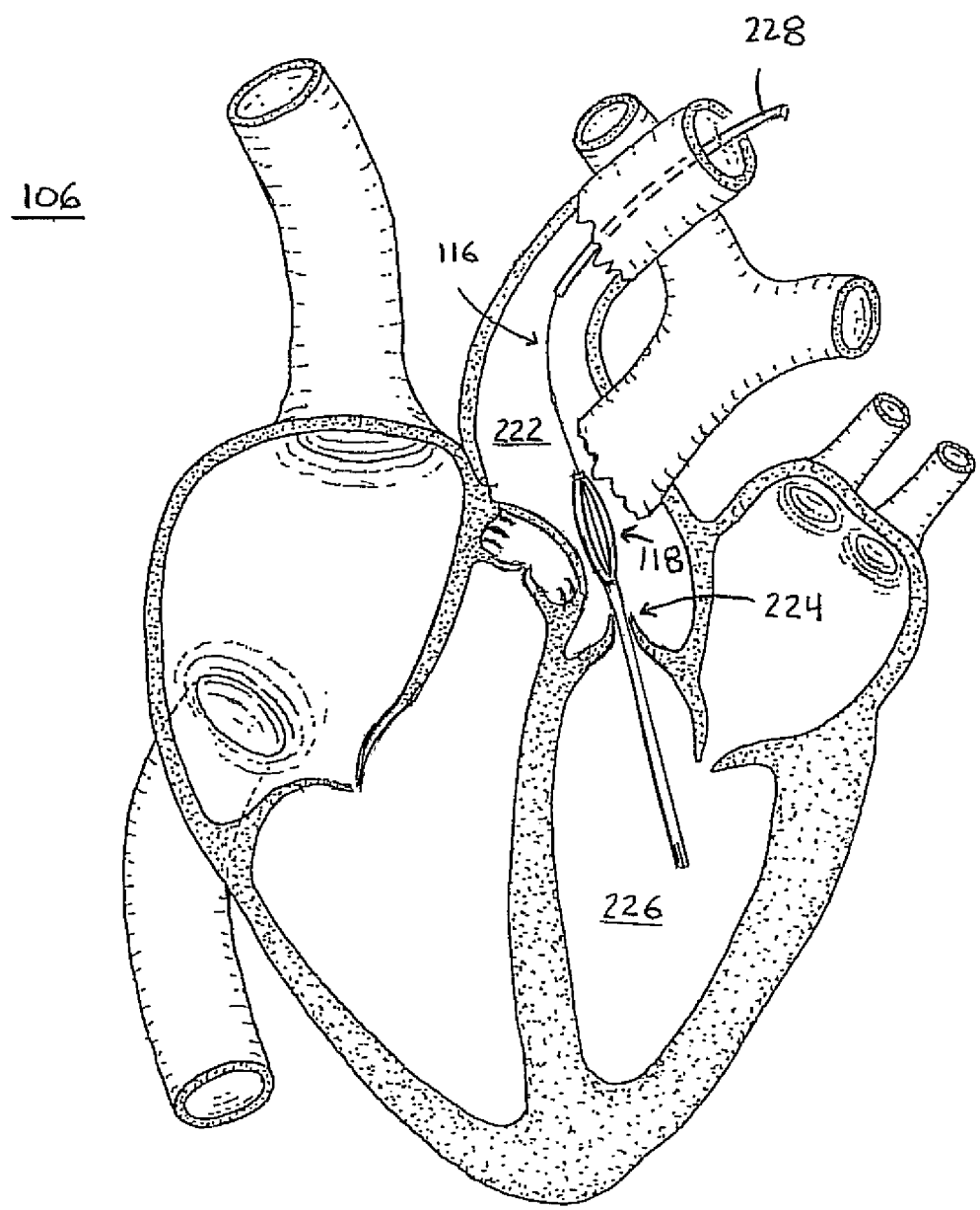
FIG. 2 depicts further detail of the heart and the pump assembly component of the cardiac-assist device.

FIG. 2 depicts a view of pump assembly 118 in heart 106. In this embodiment, pump assembly 118 is disposed in ascending aorta 222. An extension or intake tube, which is coupled to the distal end of pump assembly 118, crosses aortic valve 224. In this manner, the pump assembly 118 draws its intake from left ventricle 226 and discharges blood into ascending aorta 222. Torque transmission line 116 is shown emerging from "introducing" tube 228. In some embodiments, the introducing tube is used to position the pump assembly at its intended position within the body.

Although the presently preferred location for pump assembly 118 is ascending aorta 118, there are other suitable locations. FIGS. 3A-3C depict three different placement locations for pump assembly 118.

FIG. 3A depicts further details of an embodiment in which pump assembly 118 is disposed in ascending aorta 222, as in FIG. 2. Inflow conduit 330, which crosses aortic valve 224 into left ventricle 226, is advantageously coupled to the suction end of pump assembly 118. In this arrangement, blood 340 is drawn through intake slots 332 of inflow conduit 330 due to the action of the spinning impeller within pump assembly 118. In some other embodiments, slots 332 are not provided; rather, one or more portions of inflow conduit 330 have an open framework or are otherwise configured to permit blood to enter. Blood 340 traverses aortic valve 224 through inflow conduit 330 and then enters pump assembly 118. Blood 340 is discharged on proximal end of pump assembly 118 into ascending aorta 222. Note that inflow conduit 330 would typically be longer, relative to the size of pump assembly 118, than is depicted in FIG. 3A. FIG. 2 depicts a more accurate representation of the relative lengths of pump assembly 118 and inflow conduit 330. It is currently known to use inflow conduits in conjunction with blood pumps, so that, in conjunction with the present disclosure, those skilled in the art will know how to incorporate an inflow conduit with cardiac-assist device 110.

FIG. 3B depicts pump assembly 118 disposed across aortic valve 224. In the embodiment that is depicted in FIG. 3B, inflow conduit 330 is not used; blood 340 directly enters the suction end of pump assembly 118 from the left ventricle. Blood 340 crosses aortic valve 224 through pump assembly 118 and is discharged into ascending aorta 222. In some alternative embodiments, inflow conduit 330 can optionally be used in this situation. On the one hand, it is disadvantageous, generally, to restrict the suction of a pump, such as by adding inflow conduit on its suction end. On the other hand, to the extent that inflow conduit 330 is expected to be about 4 inches in length, it is less likely for the combination of the pump assembly 118 and inflow conduit 330 to be displaced from aortic valve 224 than would be the case if pump assembly 118 alone were disposed across the aortic valve.

FIG. 3C depicts pump assembly 118 disposed in left ventricle 226. Outflow conduit 334, which crosses aortic valve 224, is advantageously coupled to the discharge end of pump assembly 118. In this arrangement, blood 340 is drawn through suction end of pump assembly 118 and discharged from the pump assembly into outflow conduit 334, which is configured identically to intake conduit 330. Blood 340 crosses aortic valve 224 through outflow conduit 334 and is discharged into ascending aorta 222 through (optional) outflow slots 336.

As previously mentioned, pump assembly 118 can be sited at locations other than the three that are depicted in FIGS. 3A-3C. For example, the pump assembly can be sited in the descending aorta or suitably-sized peripheral vessels. It is notable that it is preferable, but not necessary, for pump assembly 118 to take suction from the left ventricle. To the extent that the pump assembly is located in a relatively more remote location (such as the descending aorta) and is to take suction from the left ventricle, a relatively longer intake conduit will be required to reach the left ventricle (than for the embodiments that are depicted in FIGS. 3A and 3C).

Thus, in most embodiments, pump assembly 118 will be sited somewhere along the route to the left side of the heart; that is, in the descending aorta, in the aortic arch, in the ascending aorta, across the aortic valve, or anywhere within the left ventricle. It is contemplated that, with certain modifications (e.g., to the impeller design, impeller rotation direction, an outflow conduit, etc.), pump assembly 118 is suitable for use in the right side of the heart or in right-side-related vasculature.

Figure 4A:
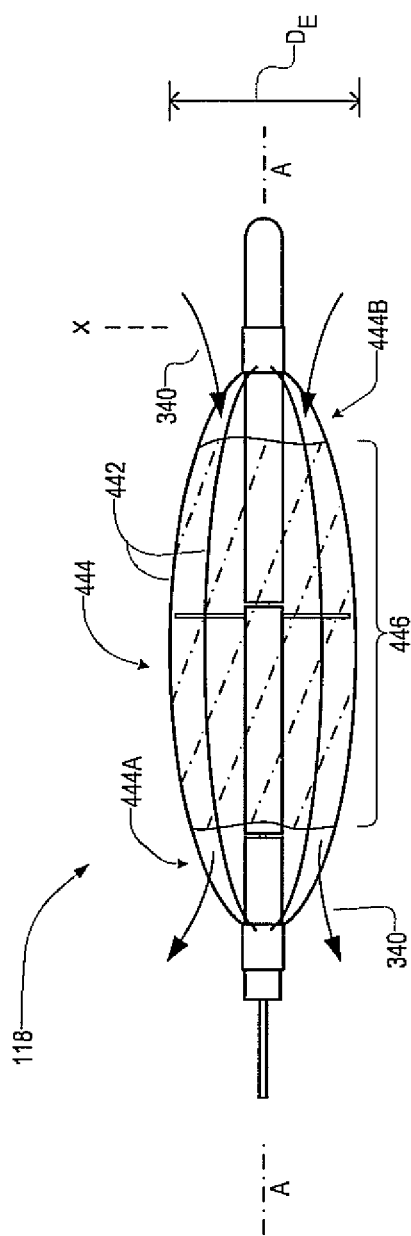
FIGS. 4A-4B depict the pump assembly in respective enlarged and contracted states.
Figure 4B:
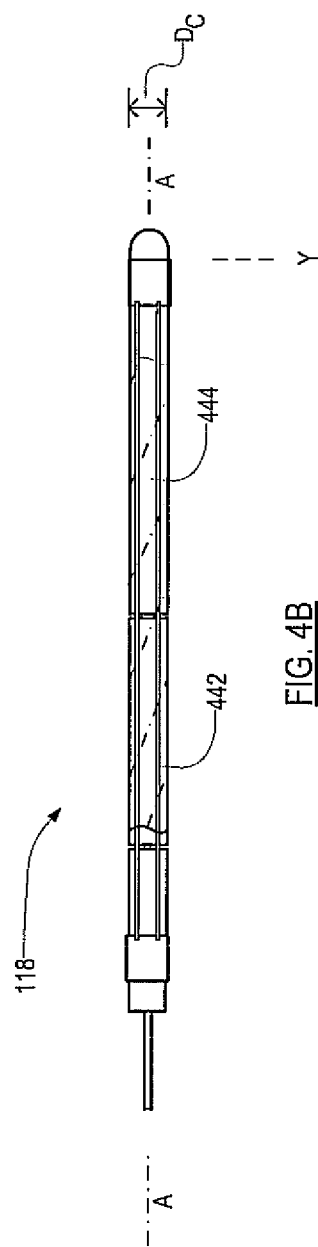

FIGS. 4A and 4B depict pump assembly 118 in respective expanded and contracted states. The expanded state is for operation (i.e., pumping blood) and the contracted state is for insertion into and withdrawal from the vascular system.

Turning now to FIG. 4A, a plurality of spaced-apart ribs 442 are axisymmetrically arranged about central axis A-A of pump assembly 118. The ribs collectively define cage or casing 444. In the embodiment that is depicted in FIG. 4A, wherein the pump assembly is in the expanded state, the ribs exhibit an arcuate shape, so that open, cage-like casing 444 adopts a typically ellipsoidal or prolate-spheroid form. In this state, the casing exhibits its maximum diameter $D_E$. This maximum or enlarged diameter is required to accommodate the impeller blades of pump assembly 118 when they are deployed for operation. As previously indicated, the ribs can exhibit any of a number of other non-planar shapes in the expanded state, as will occur to those skilled in the art in view of the present disclosure.

Casing 444 provides one or more of the following functions:
   it prevents the spinning impeller blades of pump assembly 118 from contacting anatomical features (see, e.g., FIG. 3B);
   it establishes structural integrity (see, description accompanying FIG. 5);
   it provides a framework for an overlying membrane.

Regarding the final point above, membrane 446 covers a portion of casing 444; end regions 444A and 444B of the casing remain uncovered. The purpose of membrane 446 is to channel or confine the blood in the vicinity of the impeller blades so that a flow field develops. Blood 340 enters and exits pump assembly 118 through respective uncovered regions 444B and 444A. In various embodiments, membrane 446 is formed from polyurethane, silicone, latex rubber, or other elastomeric compounds.

In some embodiments, ribs 442 are formed in such a way (e.g., processing, materials of fabrication, etc.) that in the absence of a restraining force, they exhibit the aforementioned non-planar (e.g., arcuate, etc.) shape, such that pump assembly 118 "naturally" assumes the expanded configuration. As a consequence, no actuating force is required to place pump assembly 118 into its operating configuration. Rather, for such embodiments, a force must be applied to restrain pump assembly 118 from expanding. A super-elastic material such as nitinol, etc., can be used to form ribs 442.

FIG. 4B depicts pump assembly 118 in its contracted state. In this state, casing 444 (and pump assembly 118) exhibits its minimum diameter $D_c$. In this state, ribs 442 are straight and substantially parallel to axis A-A of pump assembly 118. Casing 444 adopts a substantially cylindrical shape.

It will be appreciated that to the extent pump assembly 118 has a relatively smaller diameter, the task of negotiating the vascular system, and in particular the aortic arch, is simplified. As a consequence, pump assembly 118 is introduced into the body (e.g., the femoral artery, etc.) in the contracted state. Typically, it is after pump assembly 118 has passed the aortic arch and entered the ascending aorta or other final locations that casing 444 is expanded for operation.

In some embodiments, pump assembly 118 is deployed into the vascular system via an "introducing" tube, such as a catheter, sheath, or the like (see, e.g., FIG. 2 at 228). In some embodiments, the introducing tube is inserted into the patient sans pump assembly 118. In embodiments in which pump assembly 118 is to be deployed in the ascending aorta or the heart, the introducing tube is inserted into the vascular system and advanced beyond the aortic arch. Only after the introducing tube has cleared the aortic arch is pump assembly inserted therein. Since pump assembly 118 is not present on initial introduction of the tube, it is easier for the tube to negotiate the vascular system. And, once the introducing tube is in place, it is expected to be easier for pump assembly 118 to be advanced to its intended deployment site through that tube than via other methods of delivery.

In some embodiments, the wall of the introducing tube provides the restraining force to maintain casing 444 in the contracted state. To expand casing 444, pump assembly 118 is simply advanced beyond the distal end of the tube. To provide this functionality, the introducing tube must possess a suitably radially-inelastic wall. Standard catheters are suitably radially-inelastic for this purpose. In conjunction with the present disclosure, it is within the capabilities of those skilled in the art to provide an introducing tube having a suitably radially-inelastic wall to maintain casing 444 in the contracted state.

To collapse casing 444 for extraction from the vascular system, pump assembly 118 is drawn back into the introducing tube (or into an "extracting" tube if the introducing tube has been removed). This is implemented, in some embodiments, by fixing one end of casing 444 so that it is immovable while the other end remains free to move. For example, in FIGS. 4A and 4B, the distal end of casing 444 is movable in the axial direction along axis A-A and the proximal end of casing 444 is non-movable.

As shown in FIG. 4A, when pump assembly is in the expanded state, the distal support ring of casing 444 is disposed at axial position x. If pump assembly 118 were to be pulled back into the distal end of the introducing tube (i.e., if it were moved to the "left" in FIG. 4), the freely movable distal end of casing 444 would permit ribs 442 to collapse as they encounter the substantially radially-inflexible tube. As the ribs collapse, they lengthen, such that the distal end of casing 444 moves to the right along axis A-A to axial position y in FIG. 4B. In some other embodiments, the proximal end of casing 444 is movable along axis A-A and the distal end of casing 444 is non-movable.

FIGS. 5 and 6A through 6D depict further details of pump assembly 118. Referring now to FIG. 5, pump assembly 118 includes proximal support housing 550, impeller hub 560, impeller blades 570, distal support 580, nose cone 582, plurality of ribs 442 that define casing 444, proximal support ring 584, distal support ring 586, and membrane 446.

Elements of pump assembly 118 are coaxial and, in some cases, linearly arranged with respect to one another. In the illustrative embodiment, proximal support housing 550, impeller hub 560, and distal support 580 are linearly arranged. Proximal support housing 550 and impeller hub 560 are coaxial with respect to drive shaft 548. Casing 444, which comprises ribs 442, proximal support ring 584, and distal support ring 586, is coaxial with respect to proximal support housing 550, impeller hub 560, and distal support 580. In some embodiments, proximal support housing 550, impeller hub 560, and distal support 580 comprise injection molded polymer.

To develop pumping action, torque from the external motor (see FIG. 1, motor 114) must be delivered to impeller blades 570. This is done by operatively coupling torque transmission line 116 to impeller blades 570. In the illustrative embodiment, this is accomplished in the following manner.

Drive shaft 548 enters proximal end of pump assembly 118. The drive shaft is the distal portion of torque transmission line 116. Drive shaft extends a relatively short distance (less than about 3 centimeters) proximal of pump assembly 118. The proximal end of drive shaft 548 transitions to a drive cable (not depicted in FIG. 5), which serves as the major portion of the torque transmission line and extends to motor 114. The drive cable is flexible to enable it to be easily advanced beyond the aortic arch, if required. In contrast, drive shaft 548 is rigid, in order that the requisite seal and bearing (described further below in conjunction with the description of FIG. 6A; see bearing 652 and seal 654) will function properly.

Drive shaft 548 passes through proximal support housing 550 to impeller hub 560. Proximal support housing 550 provides a non-rotating support surface for the proximal support ring 584, thereby supporting the proximal end of casing 444. Since casing 444 does not rotate, it cannot couple to a rotating surface, such as impeller hub 560.

Since proximal support housing 550 does not rotate but impeller hub 560 does, they are separated by gap 556. And since drive shaft 548 passes through proximal support housing 550, a bearing must be provided within the housing to accommodate the rotational movement of drive shaft 548. A seal must also be provided within proximal support housing 550 to prevent blood from entering. If blood were to enter housing 550 in the small gap between drive shaft 548 and the bore that accepts it, the blood would be hemolyzed by the action of drive shaft 548. Further details of this portion of pump assembly 118, which is demarcated in FIG. 5 as region A, is depicted FIG. 6A.

Turning now to FIG. 6A, drive shaft 548 enters proximal support housing 550 and passes through bearing 652. Seal 654 is disposed at the distal end of housing 550. As previously described, bearing 652 accommodates rotation of drive shaft 548 and seal 654 prevents blood from entering proximal support housing 550. The bore of bearing 652 provides substantially all of the structural rigidity for impeller blade 570/impeller hub 560. Materials suitable for bearing 652 include, without limitation, low friction polymers, such as Teflon® (polytetrafluoroethylene), Torlon® (polyamide-imide), Rulon® (propriety polytetrafluoroethylene-based compounds), Vespel® (thermoplastic polyimide) sleeve bearings, biocompatible bearings and the like. In some embodiments, polyurethane or silicon lip seals or o-rings are used as seal 654.

In some embodiments, drive shaft 548 is formed as an integral part of impeller hub 560. In some other embodiments, impeller hub 560 is formed around drive shaft 548. In any case, drive shaft 548 is rigidly coupled to impeller hub 560 to efficiently drive impeller blades 570. Drive shaft 548 (and the drive cable) is formed of stainless steel or other materials having specific dimensions, hardness, surface finish, and radiused edges for damage-free seal insertion. Surface finish will be specified by the bearing or seal manufacturer to ensure compatibility with bearing 652 and seal 654.

Returning to FIG. 5, impeller blades 570 are depicted in a deployed position. They extend substantially orthogonally from impeller hub 560. Further details of this portion of pump assembly 118, which is demarcated in FIG. 5 as region B, are depicted in FIG. 6B. An alternative embodiment of the impeller is described later in conjunction with FIG. 7.

FIG. 6B depicts distal end of impeller hub 560. Slot 664 receives impeller blades 570. Impeller blade 570A is depicted within slot 664 in a stowed position and impeller blade 570B is depicted in a deployed position. The impeller blades rotate about axle pin 672 to deploy or retract. Impeller blades 570A and 570B are formed from materials such as, without limitation, injection molded polymer or stainless steel. Axle pin 672 is formed from a material such as 300 series stainless steel. It is to be understood that the impeller blades will normally deploy and retract in unison; the stowed/deployed configuration of FIG. 6B is depicted for pedagogical purposes.

In the illustrative embodiment, axle pin 672 is near distal end of impeller hub 560 so that impeller blades 570 open from proximal to distal. In some other embodiments, axle pin 672 is substantially proximal of impeller blades 570 so that the blades open from distal to proximal.

In some embodiments, impeller blades 570 are biased to deploy; that is, they must be restrained to be kept within impeller hub 560. In some embodiments, the biasing force partially deploys the impeller blades while the rapid rotation of impeller hub 560 completes the deployment. To the extent that impeller blades 570 are biased to at least partially deploy, ribs 442 restrain impeller blades 570 from deploying when casing 444 is in the contracted state.

Returning again to FIG. 5, casing 444 is advantageously supported at its distal end. Such support is provided by distal support 580, which receives distal support ring 586. Like proximal support housing 550, the distal support is not rotating. Since, however, impeller hub 560 is rotating, the hub and distal support 580 are separated by gap 574. Because drive shaft 548 does not extend beyond impeller blades 570, a pin or other means is required to couple distal support 580 to impeller hub 560. Further details of this portion of pump assembly 118, which is demarcated in FIG. 5 as region C, are depicted in FIG. 6C.

Figure 6D:
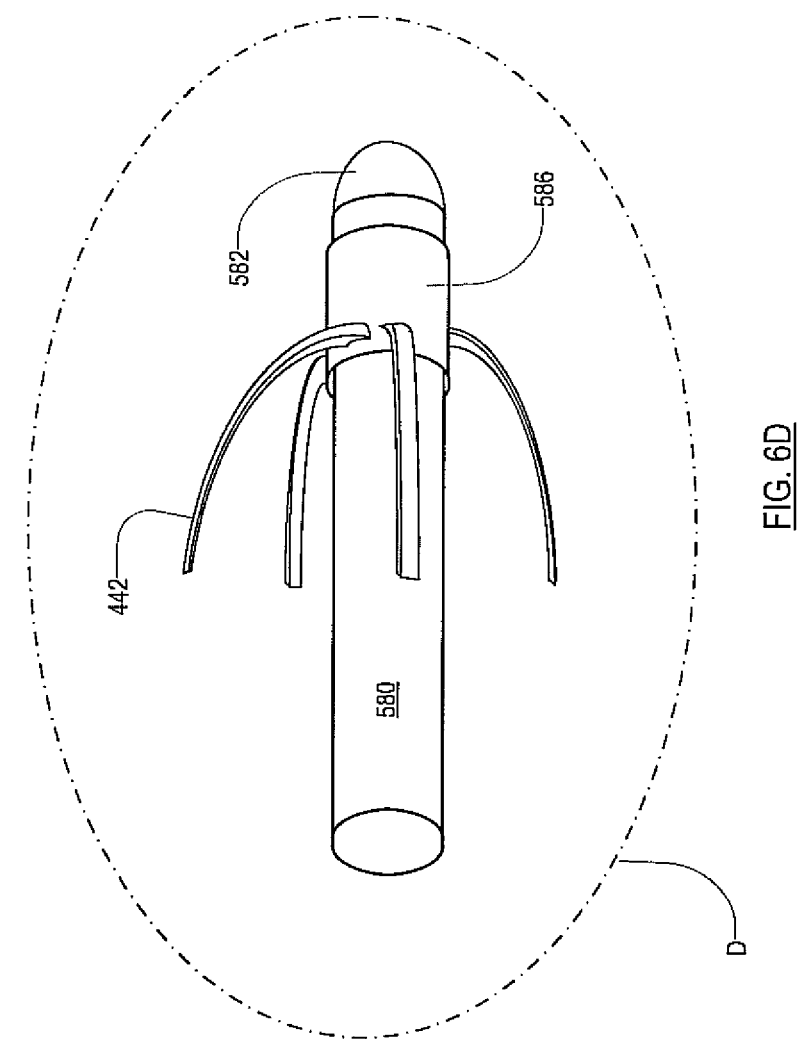
FIG. 6D depicts further detail of region "D" of the pump assembly shown in FIG. 5.
Figure 6C:
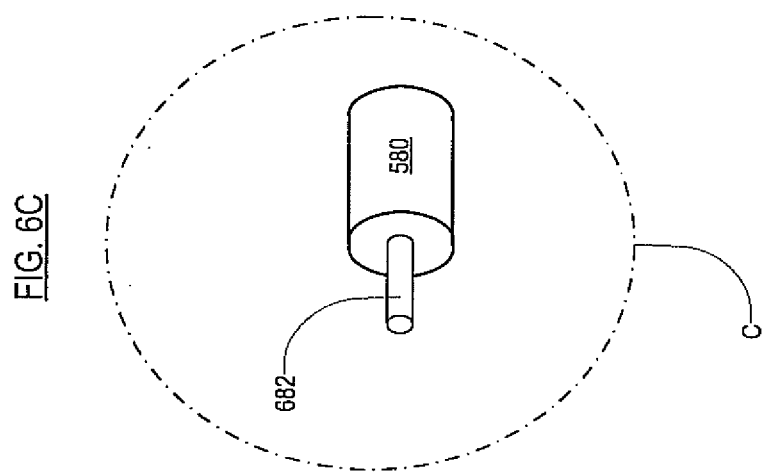
FIG. 6C depicts further detail of region "C" of the pump assembly shown in FIG. 5.

Referring now to FIGS. 6B and 6C, locating pin 682 depends from proximal end of distal support 580. Pin 682 couples proximal end of support 580 to distal end of impeller hub 560 at bore 669. Disposed within the distal end of impeller hub 560 are bearing 666 and seal 668. Since, as previously disclosed, impeller hub 560 is rotating and distal support 580 is not, bearing 666 is required to accommodate this differential movement. Seal 668 prevents leakage of blood into impeller hub 560 at bore 669. In some embodiments, bearing 666 and seal 668 are formed of the same materials as bearing 652 and seal 654, respectively.

The distal end of distal support 580 terminates in nose cone 582, which provides an atraumatic surface that is contoured for easy insertion and navigation through a patient's vascular system.

FIG. 6D depicts further detail of the distal end of pump assembly 118, demarcated in FIG. 5 as region D.

As previously described, in some embodiments, one of either the proximal end or the distal end of casing 444 is movable in an axial direction. This facilitates the expansion and contraction of the casing. In embodiments in which casing 444 is to be collapsed simply by the act of inserting the proximal end of pump assembly 118 into an introduction/extraction catheter, then it is advantageous (but not necessary) for the distal end of casing 444 to be the movable end. In such embodiments, distal support ring 586 is coupled to distal support 580 so that it is able to readily slide along the support in either direction.

In some embodiments, such as depicted in FIG. 5, sheath 590 depends from the proximal end of proximal support ring 584. The sheath, which runs substantially the full length of torque transmission line 116, is used for one or more of the following purposes:

During insertion of pump assembly 118 into a patient, tension can be placed on the sheath to maintain casing 444 in the contracted state. In such embodiments, proximal support ring 584 is movable and distal support ring 586 is fixed.

Pressurized fluid (e.g., lubricant, etc.) can be delivered to pump assembly 118 to provide a flow out of at least seal 654 to prevent leakage into that seal.

With regard to the latter point above, it is important to prevent blood from leaking into any of the seals of pump assembly 118. To that end, in some embodiments, a pressurized fluid, such as a lubricant, is provided to seal 654 and, optionally, to seal 668. As described above, to deliver fluid to seal 654, the fluid can be delivered in sheath 590. The pressurize fluid permeates the drive cable (which leads to drive shaft 548). The fluid wets the surface of drive shaft 548 and is carried into proximal support housing 550. The fluid passes through the small clearance between drive shaft 548 and bearing 652 and flows out through seal 654 at gap 556 (see FIG. 6A).

Either of several approaches can be used to provide presurized fluid to seal 668 at the distal end of impeller hub 560. In particular, in some embodiments, drive shaft 548 is hollow (not depicted) for conducting fluid. In embodiments in which the blades collapse into the impeller hub, the hub will include impeller-blade receiving slot 664. The fluid must be channeled around this slot, so a cross channel (not depicted) leads from the axially-disposed bore in drive shaft 548 to a second, non-axially disposed channel (not depicted) that leads to seal 668.

In some other embodiments, rather than conducting fluid through impeller hub 560, fluid is stored under pressure in a reservoir (not depicted) that is disposed in distal support 580. In some embodiments, this fluid fills a cavity that is defined between the proximal end of distal support 580 and an internal plug (not depicted). A spring, which is positioned behind the plug within the distal support, pressurizes the fluid. For such embodiments, locating pin 682 includes a bore that communicates with the pressurized fluid reservoir. In this fashion, fluid is delivered through the bore in locating pin 682 to seal 668 in the distal end of impeller hub 560.

Figure 7:
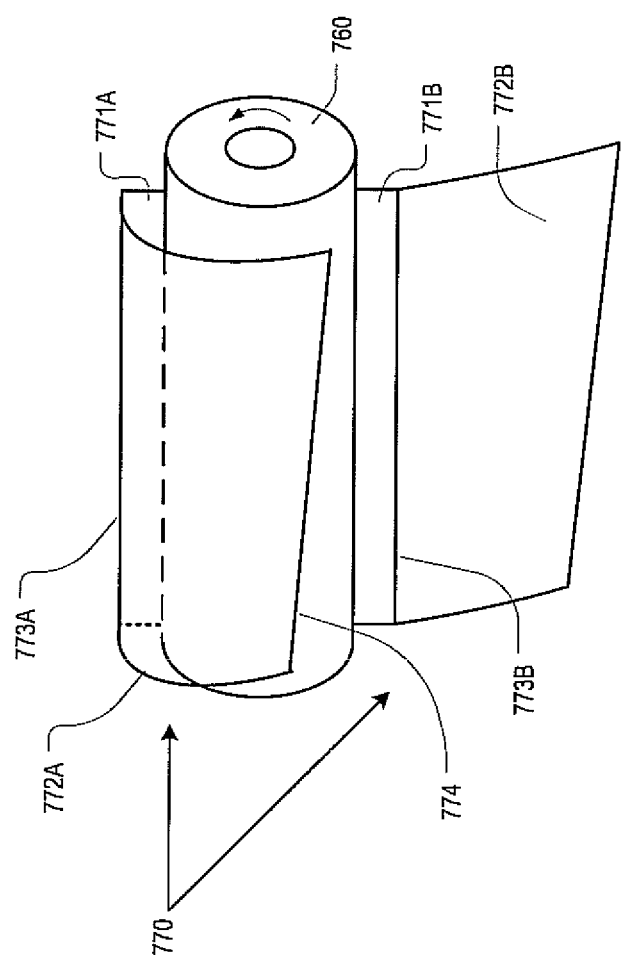
FIG. 7 depicts an alternative embodiment of a pump impeller for use in conjunction with the pump assembly.

FIG. 7 depicts an alternate embodiment of an expandable/collapsible impeller for use in conjunction in the illustrative embodiment of the present invention. As depicted in FIG. 7, impeller 770 includes two diametrically-opposed blade stubs 771A and 771B and two blades 772A and 772B. In the illustrative embodiment, each blade stub 771A and 771B extends substantially perpendicularly from and is axially aligned with impeller hub 760. Blade 772A is pivotably coupled to blade stub 771A at hinge 773A. Likewise, blade 772B is pivotably coupled to blade stub 771B at hinge 773B. For convenience, these elements will be generically referenced as "blade stub(s) 771," "blade(s) 772," and "hinge(s) 773."

Unlike impeller blades 570A and 570B, which retract into the impeller hub when the pump assembly is in the contracted state, impeller blades 770 simply hug the surface of impeller hub 760. Blade 772A is depicted in a collapsed or retracted state. To deploy for operation, impeller blades pivot about hinge 773. Blade 772B is depicted in the deployed or expanded state.

In some embodiments, impeller blades 772 are biased to deploy, such as by spring loading hinges 773. In such embodiments, when pump assembly 118 emerges from an introducing tube, for example, the casing and impeller blades expand. In some other embodiments, hinges 773 are oriented so that impeller blades 772 are deployed as a consequence of the hydrodynamic Coriolis forces that arise when impeller hub 760 is rotated for operation. For the arrangement that is depicted in FIG. 7, rotation in the indicated direction will cause blades 772 to deploy. Conversely, when rotated in the opposite direction, the hydrodynamic forces push blades 772 toward the collapsed position. Hinge details are not provided in FIG. 7; it is within the capabilities of those skilled in the art, in light of the present disclosure, to design and implement hinges to provide the desired functionality.

When impeller blades 772 are collapsed, the minimum diameter of the pump assembly, excluding the casing (hereinafter "package diameter"), is the distance between hinges 773A and 773B. The width of each blade 772 can equal the package diameter, so that when blades 772 are deployed, their total span (i.e., the diameter of the blade circle) can reach three times the package diameter.

In the illustrative embodiment, blades 772 are shown with twist. That is, edge 774 is skewed. A blade having twist can push blood axially. In some other embodiments, blades 772 do not have twist. Blades without twist will tend to push the blood radially outward in the manner of a centrifugal pump. Blades without twist are advantageously located near an opening through casing 444 (see, e.g., FIG. 4A, region 444A) so that the radially-flowing blood flows out of pump assembly 118. In some embodiments, holes (not shown) are provided through membrane 446 to facilitate the passage of radially-flowing blood out of pump assembly 118.

It is to be understood that the above-described embodiments are merely illustrative of the present invention and that many variations of the above-described embodiments can be devised by those skilled in the art without departing from the scope of the invention. For example, in this Specification, numerous specific details are provided in order to provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

What is claimed is:

1. A temporary cardiac-assist device having a pump assembly that is physically adapted to be driven by a torque transmission line, wherein the pump assembly comprises:
   a drive shaft, wherein the drive shaft is a distal portion of the torque transmission line;
   a proximal support housing, wherein the drive shaft passes through the support housing, and wherein the support housing does not rotate;
   an impeller hub, wherein the impeller hub is distal to and axially aligned with the support housing and is operatively coupled to the drive shaft, wherein no portion of the torque transmission line extends beyond the impeller hub;
   an impeller blade that depends from the impeller hub;
   a casing for enclosing the impeller blade, wherein the casing has an expanded state and a collapsed state;
   a distal support, wherein distal support is distal to, coupled to, and axially aligned with the impeller hub, and wherein the distal support is not subjected to an axial load when the casing reconfigures from the collapsed state to the expanded state.

2. The cardiac-assist device of claim 1 wherein the casing comprises a plurality of ribs that terminate, at a proximal end of the casing, in a proximal support ring and that terminate, at a distal end of the casing, in a distal support ring.

3. The cardiac-assist device of claim 2 wherein the proximal support ring encircles the proximal support housing and the distal support ring encircles the distal support.

4. The cardiac-assist device of claim 2 wherein the proximal support ring is immovable and wherein the distal support ring is unconstrained and slideable along the distal support.

5. The cardiac-assist device of claim 2 wherein the proximal support ring is unconstrained and slideable along the proximal support housing and wherein the distal support ring is immovable.

6. The cardiac-assist device of claim 1 further comprising a distal-most bearing, wherein the distal-most bearing is disposed in the impeller hub.

7. The cardiac-assist device of claim 6 wherein the distal-most bearing couples the rotating impeller hub to the distal support, which does not rotate.

8. The cardiac-assist device of claim 7 wherein the impeller blade is not twisted and wherein there is an opening in the membrane to permit radially-directed flow that is generated by the impeller blade to exit the casing, wherein the opening and the impeller blade have substantially the same axial displacement along a rotational axis of the cardiac-assist device.

9. The cardiac-assist device of claim 1 further comprising a flexible drive cable, wherein a proximal end of the drive cable is operatively coupled to a motor and wherein a distal end of the drive cable is operatively coupled to the drive shaft, wherein the drive cable and the drive shaft collectively form the torque transmission line.

10. The cardiac-assist device of claim 9 wherein the pump assembly has no more than two seals, wherein the seals prevent contact of blood with the drive shaft.

11. The cardiac-assist device of claim 9 further comprising the motor.

12. The cardiac-assist device of claim 1 wherein a proximal end of the casing is immovably coupled to the proximal support housing and a distal end of the casing is movably coupled to the distal support.

13. The cardiac-assist device of claim 1 wherein a proximal end of the casing is movably coupled to the proximal support housing and a distal end of the casing is immovably coupled to the distal support.

14. The cardiac-assist device of claim 1 wherein the impeller hub comprises an opening that receives the impeller blade when the casing is in the collapsed state.

15. The cardiac-assist device of claim 1 wherein the impeller blade is physically adapted to deploy from a non-operational state to an operational state in which the impeller blade is substantially orthogonal to a rotational axis thereof and is disposed near the longitudinal midpoint of the casing.

16. The cardiac-assist device of claim 1 wherein the distal support housing has a cylindrical shape and wherein the second end of the casing comprises a ring that receives the distal support housing in sliding engagement.

17. A cardiac-assist device having a pump assembly, wherein the pump assembly comprises:
   a drive shaft;
   an impeller hub, wherein the impeller hub is operatively coupled to the drive shaft for rotation, and wherein the drive shaft does not extend distal to an impeller blade that depends from the impeller hub;
   a distal support, wherein distal support is non-rotating, distal to, coupled to, and axially aligned with the impeller hub; and
   a distal bearing, wherein the distal bearing accommodates the coupling of the rotating impeller hub to the non-rotating distal support, and wherein the distal bearing is not subjected to an axial load when a casing that encloses the impeller blade is expanded.

18. The cardiac-assist device of claim 17 further comprising a proximal support housing that is proximal to and axially-aligned with the impeller hub.

19. The cardiac-assist device of claim 18 further comprising a proximal bearing, wherein the proximal bearing accommodates passage of a drive cable through the proximal support housing.

20. The cardiac-assist device of claim 19 wherein the pump assembly has no bearings other than the proximal bearing and the distal bearing.

21. The cardiac-assist device of claim 17 wherein the distal bearing is disposed in the impeller hub.

22. The cardiac-assist device of claim 17 further comprising a pin, wherein the pin is received by the distal support and couples the impeller hub to the distal support.

23. A cardiac-assist device comprising:
a proximal support housing;
an impeller hub, wherein the impeller hub is distal to and axially aligned with the support housing;
an impeller blade coupled to the impeller hub;
a torque transmission line, wherein the torque transmission line is operatively coupled to the impeller hub to rotate the impeller hub during operation;
a distal support, wherein distal support is distal to, coupled to, and axially aligned with the impeller hub, and wherein the distal support does not rotate; and
a casing for enclosing the impeller blade, wherein the casing expands from a collapsed state without the application of an axial load to the distal support, and wherein a proximal end of the casing is supported by the proximal support housing and a distal end of the casing is supported by the distal support.

24. The cardiac-assist device of claim 23 and further wherein at least one of the proximal end of the case and the distal end of the casing is slidable along the distal support.

25. A cardiac-assist device comprising:
a proximal support housing;
an impeller hub, wherein the impeller hub is distal to and axially aligned with the support housing;
an impeller blade that depends from the impeller hub, wherein the impeller blade is physically adapted to generate axial flow;
a distal support, wherein distal support is distal to, coupled to, and axially aligned with the impeller hub, and wherein the distal support does not rotate;
a casing for enclosing the impeller blade, wherein the casing has an expanded state and a collapsed state;
a torque transmission line, wherein the torque transmission line is operatively coupled to the impeller hub and is not subject to an axial load when the casing reconfigures from the collapsed state to the expanded state.

26. A cardiac-assist device having a pump assembly, wherein the pump assembly is physically adapted to be driven by a torque-transmission line, wherein the pump assembly comprises
a rotatable impeller hub, wherein the impeller hub is operatively coupled to the torque transmission line;
a non-rotating proximal support housing and a non-rotating distal support that are axially aligned with and flank the impeller hub;
a casing for enclosing an impeller blade, wherein the impeller blade depends from and rotates with the impeller hub;
a proximal support ring is disposed at the proximal end of the casing and is received by the proximal support housing; and
a distal support ring is disposed at the distal end of the casing and is received by the distal support, and wherein one of the distal support ring or the proximal support ring is coupled to its respective support so that it is able to slide along the support in either direction, wherein movement in the axial direction of the one movable ring enables the casing to expand and contract.

* * * * *